(12) United States Patent
Attinger

(10) Patent No.: US 11,471,036 B2
(45) Date of Patent: Oct. 18, 2022

(54) DEFORMABLE BLADE FOR A LARYNGOSCOPE

(71) Applicant: KARL STORZ SE & Co. KG, Tuttlingen (DE)

(72) Inventor: Jürg Attinger, Stein am Rhein (CH)

(73) Assignee: KARL STORZ SE & CO. KG, Tuttlingen (DE)

( * ) Notice: Subject to any disclaimer, the term of this patent is extended or adjusted under 35 U.S.C. 154(b) by 741 days.

(21) Appl. No.: 16/507,928

(22) Filed: Jul. 10, 2019

(65) Prior Publication Data
US 2020/0054204 A1    Feb. 20, 2020

(30) Foreign Application Priority Data

Jul. 12, 2018 (DE) .................. 10 2018 116 885.3

(51) Int. Cl.
| | | |
|---|---|---|
| A61B 1/267 | (2006.01) | |
| A61B 1/005 | (2006.01) | |
| A61B 1/008 | (2006.01) | |
| A61B 1/01  | (2006.01) | |
| A61B 1/24  | (2006.01) | |

(52) U.S. Cl.
CPC .............. *A61B 1/267* (2013.01); *A61B 1/008* (2013.01); *A61B 1/0052* (2013.01); *A61B 1/0055* (2013.01); *A61B 1/0057* (2013.01); *A61B 1/01* (2013.01); *A61B 1/24* (2013.01)

(58) Field of Classification Search
CPC ..... A61B 1/267; A61B 1/0052; A61B 1/0055; A61B 1/0057; A61B 1/008; A61B 1/01; A61B 1/24; A61M 16/0488; A61M 16/0418; A61M 2025/0915; A61M 25/09025; A61M 25/0147
See application file for complete search history.

(56) References Cited

U.S. PATENT DOCUMENTS 4,360,008 A * 11/1982 Corazzelli, Jr. ........ A61B 1/267
                                                          600/197
10,974,005 B1 * 4/2021 Sun .................... A61M 16/0418
(Continued)

FOREIGN PATENT DOCUMENTS

| DE | 10 2016 113 498 A1 | 1/2018 |
|---|---|---|
| FR | 2 821 736 A1 | 9/2002 |

(Continued)

*Primary Examiner* — Howard D Brown, Jr.
(74) *Attorney, Agent, or Firm* — McGlew & Tuttle, P.C.

(57) ABSTRACT

A laryngoscope blade (30) includes a blade proximal end (32), to be articulated to a handle (20), a blade distal end (38), a patient tongue side (34), a patient palate side (36), a plurality of adjacent rigid elements (40, 50, 60, 70) extending from the tongue side to the palate side, a plurality of joints (46, 56, 66) articulately connecting two of the adjacent rigid elements, and a force-transmitting mechanism (80), with a proximal end (82) and a distal end (87). The force-transmitting mechanism distal end is mechanically connected to the blade distal end. The force-transmitting mechanism is movable relative to the rigid elements in a longitudinal direction. The force-transmitting mechanism proximal end is mechanically couplable to the handle such that, by pivoting of the handle relative to the blade proximal end, the force-transmitting mechanism is moved relative to the blade proximal end.

13 Claims, 5 Drawing Sheets

(56) References Cited

U.S. PATENT DOCUMENTS

| | | | |
|---|---|---|---|
| 2010/0261968 A1 | 10/2010 | Nearman et al. | |
| 2013/0310650 A1 | 11/2013 | Christopher et al. | |
| 2015/0031957 A1 | 1/2015 | Chen et al. | |
| 2016/0058276 A1* | 3/2016 | Ramos Da Silva | A61B 1/07 600/196 |
| 2018/0020906 A1* | 1/2018 | Nettelroth | A61B 1/00105 600/190 |
| 2020/0368474 A1* | 11/2020 | Sun | A61M 16/0488 |

FOREIGN PATENT DOCUMENTS

| | | |
|---|---|---|
| KR | 20080056779 A | 6/2008 |
| WO | 97 30 626 A1 | 8/1997 |
| WO | 2011 150 469 A1 | 12/2011 |

\* cited by examiner

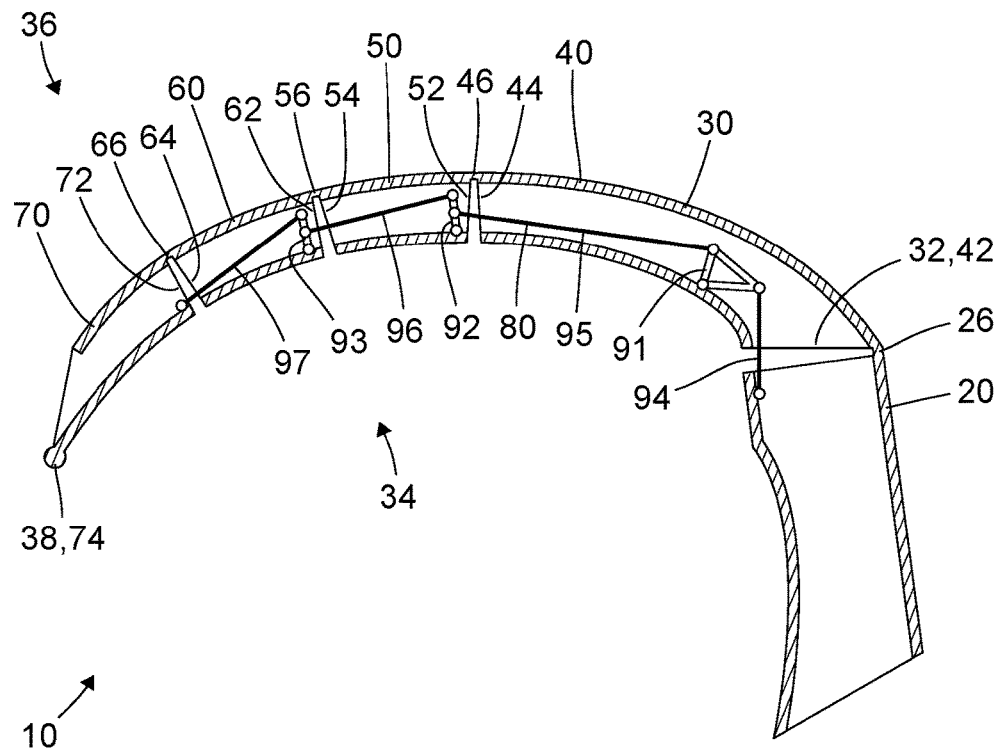
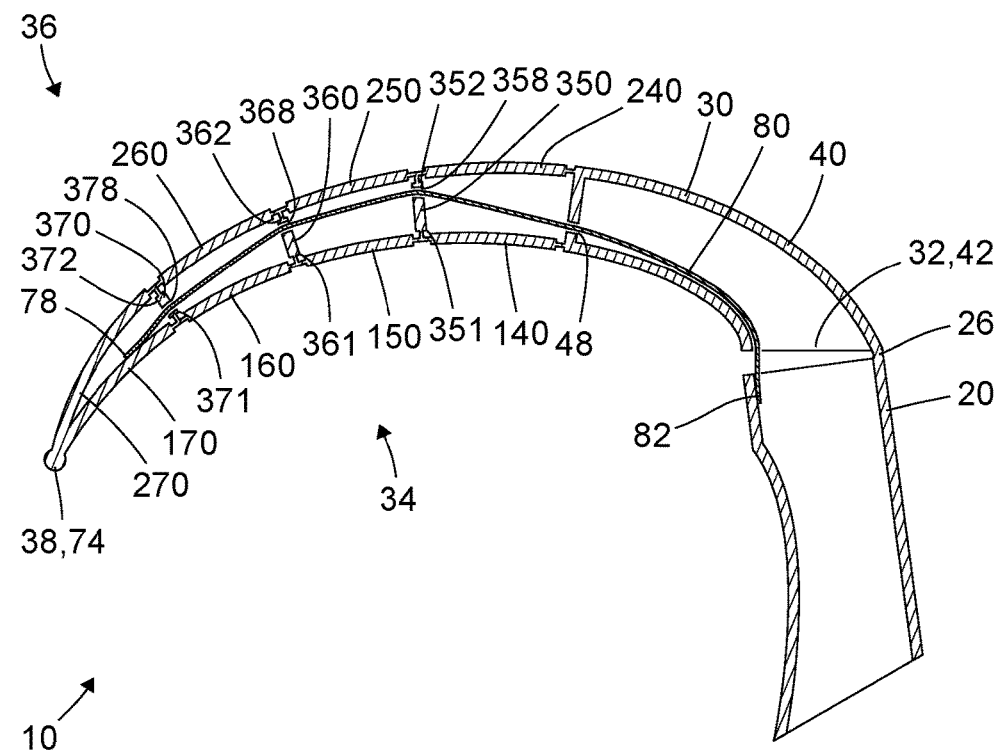

DEFORMABLE BLADE FOR A LARYNGOSCOPE

CROSS REFERENCE TO RELATED APPLICATIONS

This application claims the benefit of priority under 35 U.S.C. § 119 of German Application 10 2018 116 885.3, filed Jul. 12, 2018.

TECHNICAL FIELD

The present invention relates to a deformable blade for an adaptable or adaptive laryngoscope, in particular for an adaptable or adaptive intubation laryngoscope, or an adaptable or adaptive laryngoscope for surgery of the larynx or for other purposes in otorhinolaryngology.

TECHNICAL BACKGROUND

To perform endotracheal intubation in anesthesia, emergency medicine and intensive care and to perform surgery of the larynx, an unobstructed access to the larynx, the vocal cords and, ultimately, the trachea is needed for the intubation or for surgical procedures. In these cases, a laryngoscope is used to push the tongue forward or in the rostral direction. A laryngoscope generally comprises a blade of greater or lesser curvature, at the proximal end of which blade a handle is arranged approximately at a right angle.

To facilitate adaptation to the anatomy of the patient, the blade is generally exchangeable. An intubation kit includes a large number of blades of different lengths and different curvatures. Moreover, different configurations of blade are available for different uses and/or to meet different preferences of the medical personnel, for example blades after Macintosh, Miller, Dörges and McCoy, the latter with a movable distal end.

A laryngoscope with a deformable distal end is also described in WO 97/30626 A1. The blade 4 of the laryngoscope has several slits 40 in a central portion 14 (page 6, lines 24 to 28; FIG. 1). The slits 40 divide the central portion 14 into segments 42, which are connected to each other only by narrow webs that act as flexure bearings (ibid.). A push rod 48 is movable inside a guide tube 46 (page 7, lines 8 and 9). A distal end of the push rod 48 is welded to a distal end 20 of the blade 4 (page 7, lines 5 and 6; FIGS. 1 to 4). An end of an actuating lever 56, configured as a slide mechanism 60 on a handle 2 of the laryngoscope, can slide the proximal end 50 of the push rod 48 in the distal direction (page 7, lines 13 to 18), in order to curve the central portion 14 of the blade 4 (page 7, lines 7 to 10; FIG. 2).

FR 2 821 736 describes a laryngoscope 1 having a handle 2 and a blade 3 (pages 11 to 14; FIGS. 1 to 3). The blade 3 comprises a plurality of segments 14 connected in an articulated manner (page 8, lines 2 to 7; FIG. 1). In order to shape the blade 3, a flexible member 15 is provided, of which the distal end 16 is connected to the distal end 9 of the blade 3, and of which the proximal end 17 is movable relative to the handle 2 (page 8, lines 9 to 14; FIG. 1).

U.S. 2010/0261968 A1 a movable laryngoscope 700 with a handle 702 and a blade 704 (paragraph [0074]; FIG. 7). The blade 704 comprises a main blade 706, a proximal blade 708 and a distal blade 710, which are connected to one another by joints 712, 714 (paragraph [0075]; FIG. 7). The handle 702 comprises a blade control component 720 or a knob 902 for controlling the curvature of the blade 704 (paragraphs [0082], [0092]; FIGS. 7 and 9). A mechanism 1206 designated as a "proximal pusher" couples the knob 902 to the proximal blade 708 at the joint 712 (paragraphs [0102], [0104]; FIGS. 13 and 14). A mechanism 1208 designated as a "distal pusher" couples a knob 1402 to the distal blade 710 at the joint 714 (ibid.).

WO 2011/150469 A1 describes a laryngoscope having a blade 1 and a handle 3. The distal end of the blade 1 is formed by a plurality of elements 7A, 7B, 7C, which are connected to one another by joints 8A, 8B, 8C (page 17, fourth last paragraph; FIGS. 3, 11, 19, 20, 21, 22 and 26). The curvature of the blade 1 can be altered by means of an actuating element 11 at the handle 3 (page 17, third last paragraph; FIGS. 3, 11, 19, 20, 21, 22 and 26). The actuating element 11 is connected to the elements 7A, 7B, 7C by means of clamping devices D, M, P (paragraph bridging pages 19 and 20; FIGS. 8, 9, 10, 22 and 24).

U.S. 2011/0144436 A1 describes a device 100 which is similar to a laryngoscope and which comprises a handle 102 and a blade 104 (paragraph [0027]; FIG. 1). The curvature of the blade 104 can be adjusted; parts of the blade 104 or the whole blade 104 can be adjusted relative to the handle 102 (paragraph [0028]).

US 2011/0319718 A1 describes a laryngoscope 100 having a handle 104 and a blade, the latter comprising a first arm component 108 and a second arm component 110 with a joint 112 between them (paragraphs [0052], [0053]; FIGS. 6A and 6B). A connecting rod or a connecting cord connects the second arm component 110 to the handle 104 in such a way that an angle between the second arm component and the handle 104 is substantially constant independently of the angle position of the first arm component (paragraph [0060]; FIGS. 6A and 6B].

SUMMARY

It is an object of the present invention to make available an improved blade for an adaptable or adaptive laryngoscope and an improved laryngoscope.

A blade for an adaptable or adaptive laryngoscope comprises a proximal end, which is connected or connectable in an articulated manner to a handle, a distal end for insertion into the throat of a patient, a first side resting on the tongue of the patient during the intended use of the blade, a second side facing toward the palate of the patient during the intended use of the blade, a plurality of rigid elements which are arranged one after another in the longitudinal direction of the blade and each extend from the first side of the blade to the second side of the blade, a plurality of joints, wherein each of the plurality of joints connects two adjacent elements in an articulated manner, and a force-transmitting mechanism for transmitting a force, with a proximal end and a distal end, wherein the distal end of the force-transmitting mechanism is mechanically connected to the distal end of the blade, wherein the force-transmitting mechanism, between its distal end and its proximal end, is movable relative to elements of the blade in the longitudinal direction of the force-transmitting mechanism, wherein the proximal end of the force-transmitting mechanism is mechanically coupled to the handle, or is provided and configured to be mechanically coupled to the handle.

A blade for an adaptable or adaptive laryngoscope comprises a proximal end, which is connected or connectable in an articulated manner to a handle for manual holding of the laryngoscope, a distal end for insertion into the throat of a patient, a first side resting on the tongue of the patient during the intended use of the blade, a second side facing toward the palate of the patient during the intended use of the blade, a plurality of rigid elements which are arranged one after another in the longitudinal direction of the blade and each extend from the first side of the blade to the second side of the blade, a plurality of joints, wherein each of the plurality of joints connects two adjacent elements in an articulated manner, and a force-transmitting mechanism for transmitting a force, with a proximal end and a distal end, wherein the distal end of the force-transmitting mechanism is mechanically connected to the distal end of the blade, wherein the force-transmitting mechanism, between its distal end and its proximal end, is movable relative to elements of the blade in the longitudinal direction of the force-transmitting mechanism, wherein the proximal end of the force-transmitting mechanism is mechanically coupled to the handle, or is provided and configured to be mechanically coupled to the handle, in such a way that, by pivoting of the handle relative to the proximal end of the blade, the force-transmitting mechanism is movable relative to the proximal end of the blade.

The blade is provided and configured in particular to form a laryngoscope which is usable for intubation or for microsurgery of the larynx or for other purposes in otorhinolaryngology. The proximal end of the blade is connected to the handle in a permanent manner, so as not to be separable without destruction, or is connected to the handle so as to be detachable or separable without destruction, in any event in an articulated manner.

The handle is provided for manual holding and guiding of the laryngoscope. The handle is therefore not just an actuating lever for controlling a curvature of the blade, but is itself provided and configured for manual holding and guiding of the laryngoscope. The handle is the only handle and forms, if need be together with a proximal region of the blade near the proximal end thereof, the only part of the laryngoscope that is touched, guided and held by medical personnel during its intended use.

Each individual element of the blade is inherently rigid, i.e. has no or substantially no elastic or plastic deformability during the intended use of the blade. Each individual joint can be configured as a flexure bearing or as a form-fit joint (for example with a shaft, an axle journal or similar in one or more corresponding bearing shells). Each joint facilitates in particular a pivoting movement about a pivot axis defined by the joint, wherein all of the pivot axes are in particular parallel to one another. The joints between the elements create a deformability of the whole blade. The curvature of the blade can be changed by pivoting the elements of the blade relative to one another.

The in particular rigid or articulated mechanical connection of the distal end of the force-transmitting mechanism to the distal end of the blade and the mobility of the force-transmitting mechanism in its longitudinal direction relative to elements of the blade between the distal end and the proximal end facilitate a variation of the curvature of the blade through movement of the force-transmitting mechanism. The coupling of the proximal end of the force-transmitting mechanism to the handle for manual holding of the laryngoscope facilitates a control of the curvature of the blade by pivoting of the handle relative to the proximal end of the blade. In this way, in particular no further lever and no further actuating mechanism is needed to facilitate a variation of the curvature of the blade. This can simplify the design and thus also the production of the blade or of the entire adaptable laryngoscope and can also make handling by medical personnel more intuitive and therefore easier and safer.

In a blade as described here, in particular in one or more or all of the plurality of joints, the spacing of the joint from the first side of the blade is greater than the spacing of the force-transmitting mechanism from the first side of the blade, wherein the force-transmitting mechanism is configured to transmit a tensile force.

In this embodiment, the spacing of the joint from the second side of the blade is smaller than the spacing of the force-transmitting mechanism from the second side.

In a blade as described here, in particular in one or more or all of the plurality of joints, the spacing of the joint from the first side of the blade is smaller than the spacing of the force-transmitting mechanism from the first side, wherein the force-transmitting mechanism is configured to transmit a pressing or shearing force.

In this embodiment, the spacing of the joint from the second side of the blade is smaller than the spacing of the force-transmitting mechanism from the second side.

In a blade as described here, either the force-transmitting mechanism is arranged near the first side of the blade and is provided and configured to transmit a tensile force, and one or more or all of the plurality of joints are arranged near the second side of the blade, or one or more or all of the plurality of joints are arranged near the first side of the blade, and the force-transmitting mechanism is arranged near the second side of the blade and is provided and configured to transmit a pressing force.

Both embodiments of the blade can facilitate an adaptation of the curvature of the blade to the use and to the patient. The arrangement of the joints at the first side of the blade, resting on the tongue of the patient during the intended use, can simplify an atraumatic configuration of the blade. However, the force-transmitting mechanism has to transmit a pressing force or shearing force in order to increase the curvature of the blade and must accordingly be flexurally stiff and/or be guided in order to prevent a lateral excursion.

The arrangement of the joints at the second side, facing toward the palate of the patient during the intended use, can facilitate a simpler configuration of the force-transmitting mechanism and of its guiding, since the force-transmitting mechanism only has to transmit a tensile force in order to increase the curvature of the blade.

In a blade as described here, in particular one or more or all of the plurality of elements have an annular cross section or a U-shaped cross section or a C-shaped cross section with respect to a section plane orthogonal to the longitudinal direction of the blade.

An annular cross section is a closed cross section, for example in the form of a circular ring or of a periphery of a square or rectangle or any other polygon, optionally with rounded corners. A U-shaped or C-shaped cross section is a cross section open at one side (for example at the first side or at the second side of the blade), for example in the form of a part of a circular ring or of an edge of a rectangle or of another polygon, optionally with rounded corners. A U-shaped cross section is present when the ends of the cross section, at the opening thereof, are arranged parallel or substantially parallel to each other. A C-shaped cross section is present when the ends of the cross section, near the opening thereof, are directed wholly or partially toward each other.

An annular or U-shaped or C-shaped cross section can facilitate an atraumatic configuration of the blade, in particular if the opening of the U-shaped or C-shaped cross section is arranged at the side facing toward the palate of the patient during the intended use. An annular or U-shaped or C-shaped cross section can moreover facilitate guiding of the force-transmitting mechanism in the interior of the cross section.

In a blade as described here, the force-transmitting mechanism is arranged in particular inside a cavity at least partially enclosed by one or more or all of the plurality of elements.

The arrangement of the force-transmitting mechanism inside the cavity can protect the force-transmitting mechanism from damage and can facilitate simple mechanical guiding of the force-transmitting mechanism.

A blade as described here moreover comprises in particular a guiding structure in one of the plurality of elements, for guiding the force-transmitting mechanism.

In a blade as described here, the guiding structure in particular comprises a sub-region of an inner surface of the element.

The guiding structure comprises, for example, a concave surface portion at the inside of the element on which the force-transmitting mechanism is guided with minimal play and minimal friction.

In a blade as described here, the guiding structure comprises in particular a channel or an eyelet.

The cross section of the channel or of the eyelet is in particular adapted to the cross section of the force-transmitting mechanism in such a way that the force-transmitting mechanism is guided in the channel or the eyelet with minimal play and minimal friction.

In a blade as described here, in particular one or more or all of the plurality of joints are configured as a flexure bearing, wherein the flexure bearing, by an elastic restoring force, defines a rest configuration of the joint.

In a blade as described here, an elastic member is provided in particular in one or more or all of the plurality of joints, wherein the elastic member, by an elastic restoring force, defines a rest configuration of the joint.

The rest configuration of the joint is in particular the configuration or angle position of the joint in which the elastic energy stored in the flexure bearing or in the elastic member is minimal Upon each excursion of the joint from its rest configuration or rest angle position, the flexure bearing or the elastic member takes up energy. Each excursion from the rest configuration or rest angle position thus takes place counter to the elastic restoring force of the flexure bearing or of the elastic member. A plurality of flexure bearings or a plurality of elastic members of the blade can be differently arranged and/or dimensioned in order to generate different restoring forces or restoring moments.

A blade as described here moreover comprises in particular one or more deflecting structures on which the force-transmitting mechanism bears or to which the force-transmitting mechanism is mechanically connected or which is part of the force-transmitting mechanism, wherein the force-transmitting mechanism runs distally from the deflecting structure in a first direction and runs proximally from the deflecting structure in a second direction, which differs from the first direction.

The first direction, in which the force-transmitting mechanism runs distally from a deflecting structure, and the second direction, in which the force-transmitting mechanism runs proximally from the same deflecting structure, differ in particular by at least 5 degrees or by at least 10 degrees or by at least 20 degrees or by at least 30 degrees or by at least 50 degrees or by at least 70 degrees. One or more deflecting structures can be arranged in some or all of the plurality of elements. Each deflecting structure can at the same time be a guiding structure or can be integrated with a guiding structure. One or more deflecting structures can in particular have the effect that spacings between the force-transmitting mechanism and the joints are of different extents, such that a force transmitted by the force-transmitting mechanism is associated with different moments at the joints.

In a blade as described here, the deflecting structure is in particular arranged near the proximal end of the blade.

A deflecting structure near the proximal end of the blade can simplify a mechanical coupling of the handle, pivotable relative to the proximal end of the blade, to the force-transmitting mechanism.

In a blade as described here, the force-transmitting mechanism has in particular a converting mechanism which converts a first force and a first path proximally from the converting mechanism into a second force and a second path distally from the converting mechanism.

In particular, the ratio between the first force and the second force and the ratio between the second path and the first path are equal, disregarding friction.

In a blade as described here, the converting mechanism comprises in particular a lever, a pulley or another gear.

A converting mechanism can facilitate a desired distribution of a force, applied to the proximal end of the force-transmitting mechanism, to the individual elements and thus defined moments at the joints between the elements or defined ratios between the moments at the individual joints.

A blade for an adaptive laryngoscope comprises a proximal end, which is connected or connectable to a handle for manual holding of the laryngoscope, a distal end for insertion into the throat of a patient, a first chain of a plurality of elements which are arranged one after another in the longitudinal direction of the blade and which are each connected in pairs in an articulated manner, which chain extends from the proximal end as far as the distal end of the blade, a second chain of a plurality of elements which are arranged one after another in the longitudinal direction of the blade and which are each connected in pairs in an articulated manner, which chain extends from the proximal end as far as the distal end of the blade, a plurality of spacer components which each connect a point at an element of the first chain to a point at an element of the second chain in an articulated manner and with a predetermined spacing, and a force-transmitting mechanism for transmitting a force, with a proximal end and a distal end, wherein the distal end of the force-transmitting mechanism is mechanically connected to the distal end of the blade, wherein the force-transmitting mechanism, between its distal end and its proximal end, is movable relative to elements of the blade in the longitudinal direction of the force-transmitting mechanism.

The blade is provided and configured in particular to form a laryngoscope which is usable for intubation or for microsurgery of the larynx or for other purposes in otorhinolaryngology. The proximal end of the blade is connected to the handle in a permanent manner, so as not to be separable without destruction, or is connected to the handle so as to be detachable or separable without destruction, in any event in an articulated manner.

The handle is provided for manual holding and guiding of the laryngoscope. The handle is therefore not just an actuating lever for controlling a curvature of the blade, but is itself provided and configured for manual holding and guiding of the laryngoscope. The handle is the only handle and forms, if need be together with a proximal region of the blade near the proximal end thereof, the only part of the laryngoscope that is touched, guided and held by medical personnel during its intended use.

The elements of the first chain and the elements of the second chain can be connected in respective pairs by flexure bearings or by form-fit joints (for example with shafts or axle journals in corresponding bearing shells). The spacer components are formed, for example, by webs, plates or frames which are arranged transversely with respect to the longitudinal direction of the blade. An end or edge portion of a spacer component is in each case connected to one or two adjacent elements of the first chain by a flexure bearing or a form-fit joint. A further opposite end or a further opposite edge portion of the spacer component is connected to one or two adjacent elements of the second chain by a flexure bearing or a form-fit joint.

The distal end of the force-transmitting mechanism is connected to the distal end of the blade in particular in a mechanically rigid or articulated manner. The proximal end of the force-transmitting mechanism can be connected to the handle, for holding the laryngoscope, in a permanent manner, so as not to be detachable or separable without destruction, or is connected to the handle so as to be detachable or separable without destruction. The proximal end of the force-transmitting mechanism is coupled in particular mechanically to the handle, such that a pivoting of the handle relative to the proximal end of the blade causes a movement of the force-transmitting mechanism relative to elements of the blade. By means of the force-transmitting mechanism, forces or moments can be exerted on the elements of the chain directly or indirectly. In this way, a curvature of the blade can be influenced by means of the force-transmitting mechanism.

A blade as described here moreover comprises in particular a guiding structure at one of the plurality of spacer components, for guiding the force-transmitting mechanism.

In a blade as described here, a first guiding structure for guiding the force-transmitting mechanism is provided in particular at a first spacer component of the plurality of spacer components, wherein a second guiding structure for guiding the force-transmitting mechanism is provided at a second spacer component of the plurality of spacer components, wherein a first ratio between the spacing of the first guiding structure from a first end of the first spacer component, which is directed toward the associated element of the first chain, and the spacing of the first guiding structure from a second end of the first spacer component, which is directed toward the associated element of the second chain, is different from a second ratio between the spacing of the second guiding structure from a first end of the second spacer component, which is directed toward the associated element of the first chain, and the spacing of the second guiding structure from a second end of the second spacer component, which is directed toward the associated element of the second chain.

The different arrangement of the guiding structures at the spacer components can have the effect that a force exerted on the proximal end of the force-transmitting mechanism causes different forces or moments at the spacer components.

A laryngoscope comprises a blade, as described here, and a handle, which is connected or connectable to the proximal end of the blade.

In a laryngoscope as described here, the proximal end of the blade is connected or connectable to the handle in particular in an articulated manner, wherein the proximal end of the force-transmitting mechanism is coupled or couplable to the handle in such a way that, by pivoting of the handle relative to the proximal end of the blade, a tensile force or a pressing or shearing force can be applied to the force-transmitting mechanism.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 9 is a schematic sectional view of a further laryngoscope;

FIG. 10 is a schematic sectional view of a further laryngoscope.

DESCRIPTION OF PREFERRED EMBODIMENTS

Figure 1:
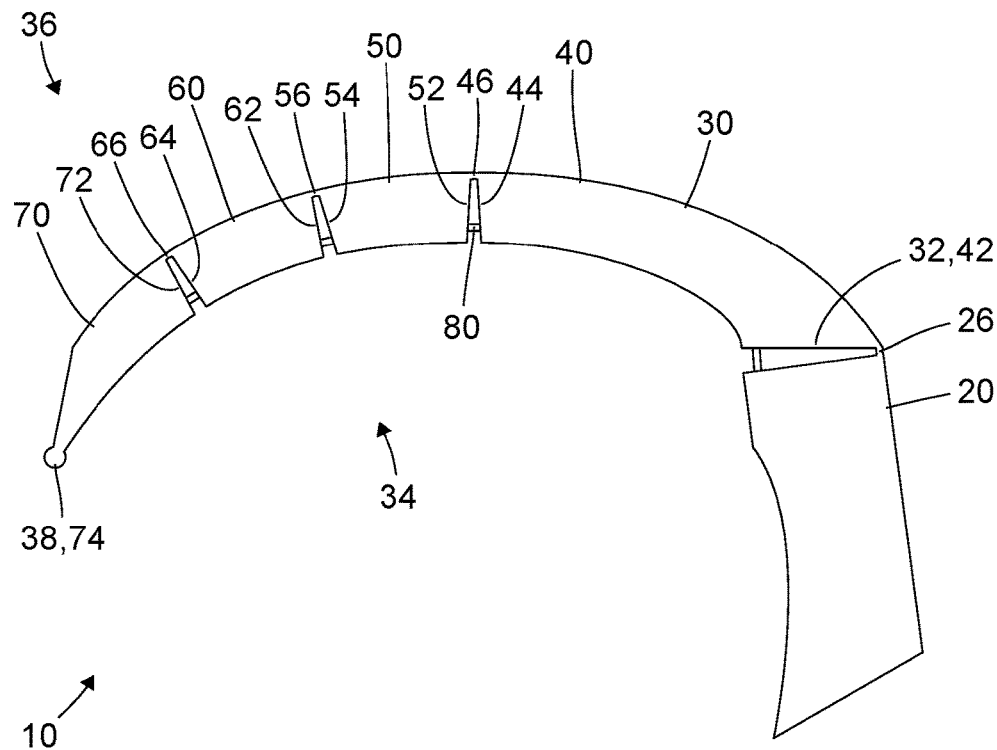
FIG. 1 is a schematic view of a laryngoscope.

Referring to the drawings, FIG. 1 shows a schematic view of a laryngoscope 10 with a handle 20 and a blade 30. The handle 20 is connected to a proximal end 32 of the blade 40 by a joint 26. The joint 26 facilitates a pivoting of the handle 20 relative to the blade 30, in particular relative to the proximal end 32 of the blade 30 about a pivot axis orthogonal to the drawing plane of FIG. 1. As is indicated in FIG. 1, the joint 26 can be configured as a flexure bearing (often also called a film hinge). Alternatively, the joint can be configured as a form-fit joint, for example with a shaft or axle journal and one or more corresponding bearing shells.

The handle 20 and the blade 30 can be connected to each other permanently and are not detachable without destruction, as in the case of the monolithic or substantially monolithic structure of the laryngoscope 10 with the flexure bearing 26 indicated in FIG. 1. Alternatively, and in contrast to this, a coupling can be provided between the handle and the blade 30 for the purpose of a mechanical connection that is releasable or separable without destruction. This coupling can be integrated with the joint 26 or can be provided at the end of the handle 20 directed toward the blade or at the end 32 of the blade 30 directed toward the handle 20.

The blade has a first first side 34 resting on the tongue and/or the tongue base of a patient during the intended use of the laryngoscope 10, and a second side 36 facing toward the palate of the patient during the intended use of the laryngoscope 10. The blade 30 extends as far as a distal end 38, which is configured in particular for atraumatic use with the greatest possible radii or curvature.

The blade 30 comprises a plurality of elements 40, 50, 60, 70, which are connected to one another by joints 46, 56, 66.

A proximal end 42 of a first element 40 forms the proximal end 32 of the blade 30. A distal end 44 of the first element 40 is connected by a first joint 46 to a proximal end 52 of a second element 50. A distal end 54 of the second element 50 is connected by a second joint 56 to a proximal end 62 of a third element 60. A distal end 64 of the third element 60 is connected by a third joint 66 to a proximal end 72 of a fourth element 70. A distal end 74 of the fourth element 70 forms the distal end 38 of the blade 30.

Each individual element 40, 50, 60, 70 of the blade 30 extends from the first side 34 resting on the tongue of the patient during the intended use of the laryngoscope 10 to the second side 36 of the blade 10 facing toward the palate of the patient during the intended use. Each element 40, 50, 60, 70 is inherently rigid, that is to say it is not deformed, or not substantially deformed, by the forces that occur during the intended use of the laryngoscope 10.

The joints 46, 56, 66 facilitate pivoting movements of adjacent elements 40, 50, 60, 70 relative to each other about associated pivot axes orthogonal to the drawing plane of FIG. 1. In the example shown, the joints 46, 56, 66 are configured as flexure bearings. Alternatively, the joints 46, 56, 66 can be configured as form-fit joints with shafts and/or axle journals in corresponding bearing shells.

The joints 46, 56, 66 are arranged at the second side 36. Between the elements 40, 50, 60, 70, gaps extend from the first side 34 as far as the joints 46, 56, 66, which gaps facilitate an enlargement of the curvature of the blade 30. Alternatively, and in contrast to the view in FIG. 1, the elements 40, 50, 60, 70 can be configured overlapping, such that no gaps are present between the elements 40, 50, 60, 70.

In the gaps between the elements 40, 50, 60, 70, a force-transmitting mechanism 80 can be seen, of which the proximal end is connected mechanically rigidly to the handle 20, and of which the distal end is connected mechanically rigidly to the fourth element 70 and thus to the distal end 38 of the blade 30. On account of its material and/or its cross section, the force-transmitting mechanism 80 is flexible, i.e. elastically and/or plastically bendable. The force-transmitting mechanism has a low elasticity in the longitudinal direction, such that it is not substantially stretched or compressed under the forces that occur during the intended use of the laryngoscope 10.

Figure 2:
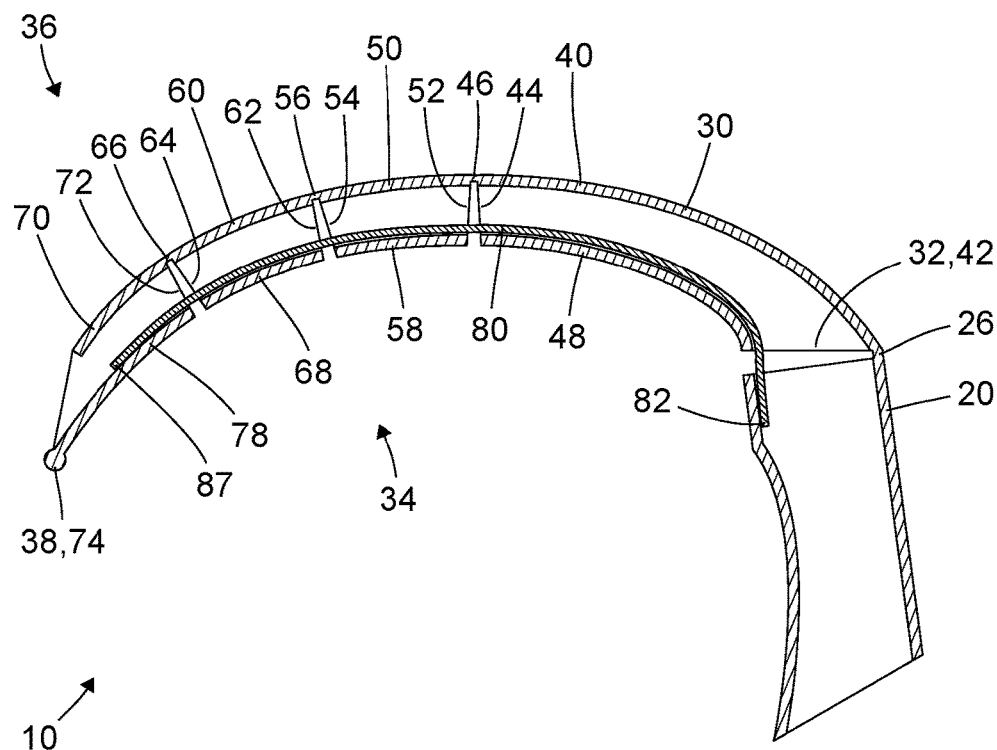
FIG. 2 is a schematic sectional view of the laryngoscope from FIG. 1.

FIG. 2 shows a schematic view of a section through the laryngoscope 10 along a plane parallel to the drawing plane of FIG. 1. The handle 20 or the blade 30 or the entire laryngoscope 10 can be configured with mirror symmetry to the section plane of FIG. 2. The configuration of the laryngoscope 10 shown in FIG. 2 corresponds to the configuration shown in FIG. 1.

It will be seen in FIG. 2 that the elements 40, 50, 60, 70 of the blade 30 each enclose a cavity, which is open at both ends. The whole blade thus has a cavity which, except for the gaps at the joints 46, 56, 66 between the elements 40, 50, 60, 70, is substantially enclosed by the elements 40, 50, 60, 70. The force-transmitting mechanism 80 is arranged in this cavity. A wall portion of each element 40, 50, 60, 70, at the first side 34 resting on the tongue of the patient during the intended use, forms a guiding structure 48, 58, 68, 78 on which the force-transmitting mechanism 80 bears.

The proximal end 82 of the force-transmitting mechanism 80 is connected to the handle 20 at a location spaced apart from the joint 26 between the handle 20 and the blade 30. In the gap between the handle 20 and the proximal end 32 of the blade 30, the force-transmitting mechanism 80 is spaced apart from the joint 26. The distal end 87 of the force-transmitting mechanism 80 is mechanically connected to the fourth element 40 at a location spaced apart from the joint 66 between the third element 60 and the fourth element 70. In the gap between the third element 60 and the fourth element 70, the force-transmitting mechanism 80 is spaced apart from the joint 26. During the intended use of the laryngoscope 10, the force-transmitting mechanism 80 transmits a tensile force from the handle 20 to the distal end 38 of the blade 30, namely to the fourth element 70 thereof. By virtue of the fact that the force-transmitting mechanism 80 is under tensile stress during the intended use of the laryngoscope 10, it bears on the guiding structures 48, 58, 68, 78, as is indicated in FIG. 2. In order to facilitate an elastic deformation of the force-transmitting mechanism, especially in the regions between the handle 20 and the blade 30 and between the elements 40, 50, 60, 70 of the blade 30, the force-transmitting mechanism is formed in particular from an elastic material and/or has a shallow cross section, for example the shape of a band.

Figure 3:
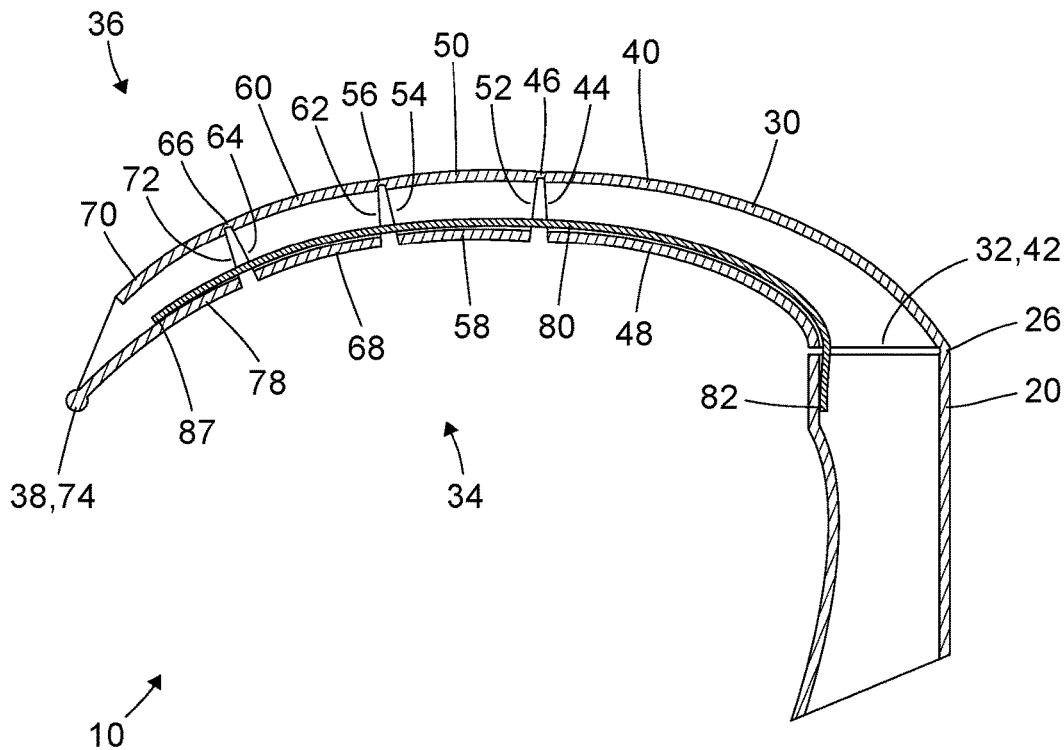
FIG. 3 is a further schematic sectional view of the laryngoscope from FIGS. 1 and 2.

FIG. 3 shows a further schematic view of a section through the laryngoscope 10 shown in FIGS. 1 and 2. The section plane of FIG. 3 corresponds to the section plane of FIG. 2. The laryngoscope 10 in FIG. 3 is shown in a configuration that differs from the configuration shown in FIGS. 1 and 2.

In the configuration shown in FIG. 3, the handle 20 of the laryngoscope 10 is pivoted toward the proximal end 32 of the blade 30, and the blade 30 is stretched by comparison with the configuration shown in FIG. 2, i.e. it has a lesser overall curvature. For this purpose, the elements 40, 50, 60, 70 are pivoted away from each other in pairs in the joints 46, 56, 66, such that the gaps between the elements 40, 50, 60, 70 are enlarged.

Figure 4:
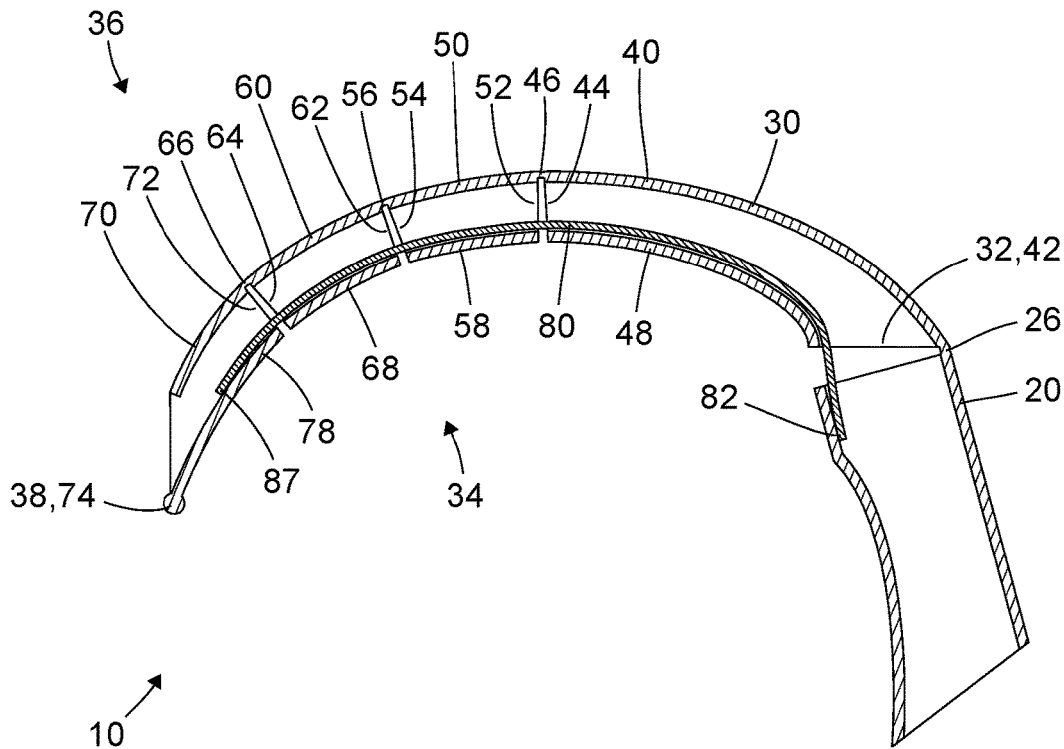
FIG. 4 is a further schematic sectional view of the laryngoscope from FIGS. 1 to 3.

FIG. 4 shows a further schematic view of a section through the laryngoscope 10 shown in FIGS. 1 to 3. The section plane of FIG. 4 corresponds to the section planes of FIGS. 2 and 3. FIG. 4 shows a configuration that differs from the configurations shown in FIGS. 1 to 3.

In the configuration of the laryngoscope 10 shown in FIG. 4, the handle 20 is pivoted away from the proximal end 32 of the blade 30, by comparison with the configurations shown in FIGS. 1 to 3. By virtue of the fact that the proximal end 82 of the force-transmitting mechanism is secured at a location spaced apart from the joint 26 between the handle 20 and the proximal end 32 of the blade 30, this pivoting movement, as far as the angled position of the handle 20 shown in FIG. 4, generates a tensile force in the force-transmitting mechanism 80 and causes a displacement of the force-transmitting mechanism 80 toward the proximal end 32 of the blade 30. This in turn causes a pivoting of the second element 50 toward the first element 40, a pivoting of the third element 60 toward the second element 50, and a pivoting of the fourth element 70 toward the third element 60. This results in the configuration shown in FIG. 4, with an increased curvature of the blade 30 by comparison with the configurations shown in FIGS. 1 to 3.

Proceeding from the configuration shown in FIG. 4, a force applied to the first side 34 of the blade 30 by the tongue or the tongue base of a patient can cause a stretching of the blade 30 to the configuration shown in FIGS. 1 and 2 and further to the configuration shown in FIG. 3, if no corresponding opposing force is applied to the handle 20. As a result, in the laryngoscope 10 shown in FIGS. 1 to 4, there is at any given time an equilibrium of the forces and moments on the handle 20 (manually generated by medical personnel) and on the elements 40, 50, 60, 70 of the blade 30 (generated by the tongue and/or tongue base of a patient).

Figure 5:
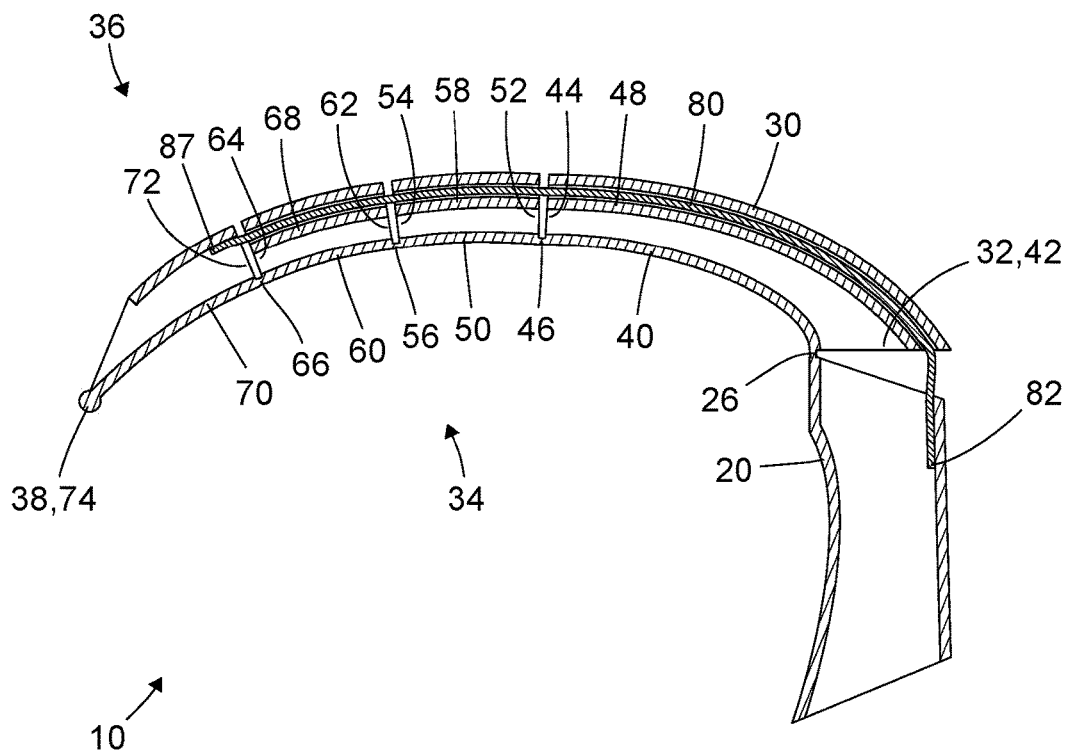
FIG. 5 is a schematic sectional view of a further laryngoscope.

FIG. 5 shows a schematic view of a section through a further laryngoscope 10 which, in terms of certain features, properties and functions, is similar to the laryngoscope shown in FIGS. 1 to 4. The section plane of FIG. 5 corresponds to the section planes of FIGS. 2 to 4. Features, properties and functions of the laryngoscope in FIG. 5 that distinguish it from the laryngoscope shown in FIGS. 1 to 4 are described below in particular.

The laryngoscope 10 shown in FIG. 5 also has a handle 20 and a blade 30 composed of a plurality of elements 40, 50, 60 and 70 which are connected to one another by joints 26, 46, 56, 66. As in the laryngoscope shown in FIGS. 1 to 4, the joints 26, 46, 56, 66 in the laryngoscope shown in FIG. 5 are also configured as flexure bearings, although alternatively, and in contrast to the view in FIG. 5, they can also be configured for example as form-fit joints with shafts or axle journals, which are mounted in corresponding bearing shells.

Unlike the laryngoscope shown in FIGS. 1 to 4, the joints 26, 46, 56, 66 in the laryngoscope shown in FIG. 5 are not arranged at the second side 36 but instead at the first side 34 resting on the tongue or the tongue base of the patient during the intended use of the laryngoscope 10.

In the same way as in the laryngoscope shown in FIGS. 1 to 4, the laryngoscope 10 shown in FIG. 5 also has a force-transmitting mechanism 80 arranged inside the cavity substantially enclosed by the elements 40, 50, 60, 70. However, the laryngoscope shown in FIG. 5 differs from the laryngoscope shown in FIGS. 1 to 4 in that the force-transmitting mechanism 80 is not arranged at the first side 34 but instead at the second side 36 of the blade 30 directed toward the palate during the intended use of the laryngoscope 10. Correspondingly, a proximal end 82 of the force-transmitting mechanism 80 is connected to the handle 20 at a location spaced apart from the joint 26 between the handle 20 and the proximal end 32 of the blade 30, and a distal end 87 of the force-transmitting mechanism 80 is mechanically connected to the fourth element 70 at a location at the second side 36 of the blade 30 spaced apart from the joint 66 between the third element 60 and the fourth element 70.

The laryngoscope 10 shown in FIG. 5 has guiding structures 48, 58, 68 for the force-transmitting mechanism 80, but in contrast to the laryngoscope shown in FIGS. 1 to 4 they merely form an interrupted channel between the elements 40, 50, 60, 70, in which channel the force-transmitting mechanism 80 is guided with minimal play and minimal friction. In contrast to the views in FIGS. 2 to 4, the laryngoscope shown in FIGS. 1 to 4 can also have channel-shaped guiding structures for the force-transmitting mechanism.

In the laryngoscope 10 shown in FIG. 5, a pivoting of the handle 20 toward the proximal end 32 of the blade 30, proceeding from the configuration shown in FIG. 5, causes a pressing or shearing force in the force-transmitting mechanism 80 and a movement of the force-transmitting mechanism 80 relative to the first element 40 of the blade 30. The guiding of the force-transmitting mechanism 80 by the channel-shaped guiding structures 48, 58, 68 and a sufficiently flexurally stiff configuration of the force-transmitting mechanism 80 prevent a lateral deviation of the force-transmitting mechanism 80 under the effect of the forces that occur during the intended use.

Figure 6:
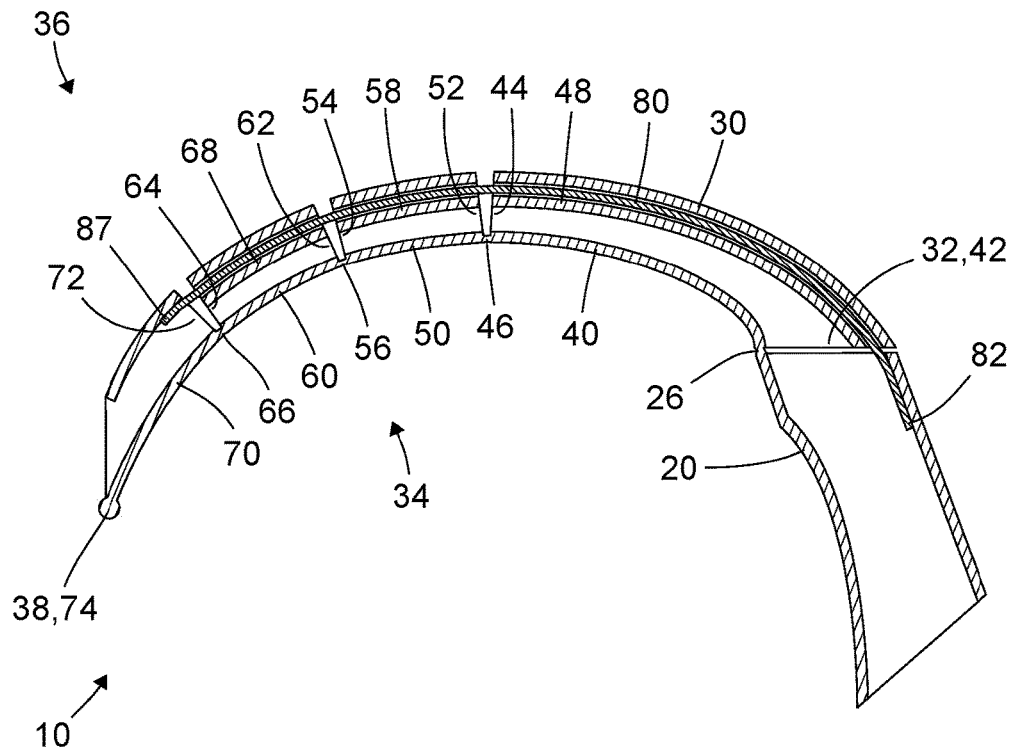
FIG. 6 is a further schematic sectional view the laryngoscope from FIG. 5.

FIG. 6 shows a schematic view of a further section through the laryngoscope shown in FIG. 5. The section plane of FIG. 6 corresponds to the section plane of FIG. 5. The configuration shown in FIG. 6 differs from the configuration of the laryngoscope 10 shown in FIG. 5.

In the configuration shown in FIG. 6, the handle 20 is pivoted toward the proximal end 32 of the blade 30. This causes a pressing or shearing force in the force-transmitting mechanism 80 and a movement of the force-transmitting mechanism 80 in the distal direction relative to the first element 40, the second element 50 and the third element 60 of the blade 30 and an enlargement of the curvature of the blade 30. Consequently, in the configuration shown in FIG. 6, this results in a widening of the gaps between the elements 40, 50, 60, 70, which gaps extend from the second side 36, directed toward the palate of the patient during the intended use, to the joints 46, 65, 66.

In the same way as in the laryngoscope shown in FIGS. 1 to 4, the curvature of the blade 30 of the laryngoscope 10 shown in FIGS. 5 and 6 can also be adjusted by pivoting the handle 20 relative to the proximal end 32 of the blade 30. A shape of the blade 30 is obtained in which an equilibrium is present between the forces and moments generated manually on the handle 20, the forces and moments acting on the elements 40, 50, 60, 70 of the blade 30 and, if appropriate, restoring forces of the joints 26, 46, 56, 66.

Figure 7:
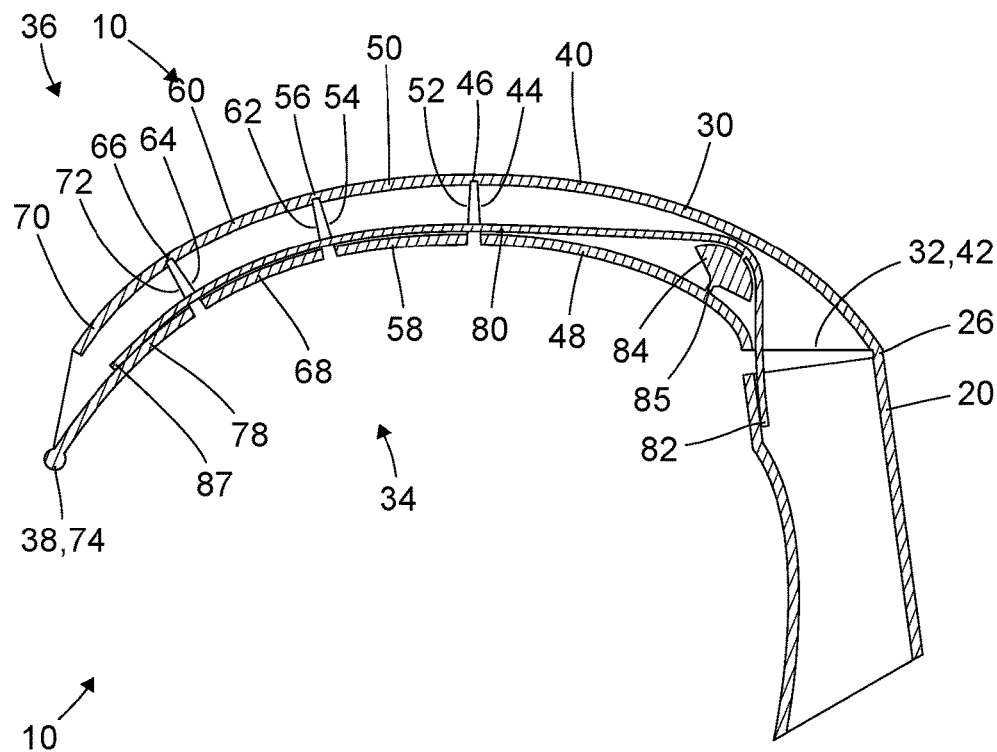
FIG. 7 is a schematic sectional view of a further laryngoscope.

FIG. 7 shows a schematic view of a section through a further laryngoscope 10 which, in terms of certain features, properties and functions, is similar to the laryngoscopes shown in FIGS. 1 to 6. The section plane of FIG. 7 corresponds to the section planes of FIGS. 2 to 6. Features, properties and functions of the laryngoscope in FIG. 7 that distinguish it from the laryngoscopes shown in FIGS. 1 to 6 are described below in particular.

The laryngoscope 10 shown in FIG. 7 differs in particular from the laryngoscope shown in FIGS. 1 to 4 in that a deflecting structure 84 is provided for the force-transmitting mechanism 80. In the example shown, the deflecting structure 84 is arranged in the first element 40 of the blade 30. The deflecting structure 84 has approximately the shape of a segment of a circle, at the circumference of which the force-transmitting mechanism 80 bears, and the tip of which is connected to an inner surface of the first element 40 by a flexure bearing 85. In the example shown, the force-transmitting mechanism 80 is also cohesively bonded at points to the deflecting structure 84.

The deflecting structure 84 causes a deflection of the direction in which the force-transmitting mechanism 80 runs. The deflecting structure 84 can reduce the friction between the force-transmitting mechanism 80 and the first element 40. Moreover, in contrast to the view in FIG. 7, the flexure bearing 85 between the deflecting structure 84 and the first element 40 can be spaced apart from the center of curvature of the surface of the deflecting structure 84 on which the force-transmitting mechanism 80 bears. This can result in a conversion in which a first force and a first path on the force-transmitting mechanism 80 proximally from the deflecting structure 84 can be converted into a second force and a second path distally from the deflecting structure 84. This conversion can be dependent on the position of the deflecting structure 84 and therefore on the position of the force-transmitting mechanism 80.

In a departure from the view in FIG. 7, the force-transmitting mechanism 80 can be connected to the deflecting structure 84 only by frictional engagement or possibly not connected to it at all. In contrast to the view in FIG. 7, the deflecting structure 84 can also be configured as a roller or wheel or as a roller segment or wheel segment or in the form of a cam disk. Moreover, in contrast to the view in FIG. 7, the deflecting structure 84 can be connected to the first element 40 via a shaft or one or more axle journals and corresponding bearing shells. In contrast to the view in FIG.

7, the deflecting structure 84 can moreover be arranged in the second element 50 or in the third element 60. Moreover, in contrast to the view in FIG. 7, a plurality of deflecting structures 84 can be provided.

Figure 8:
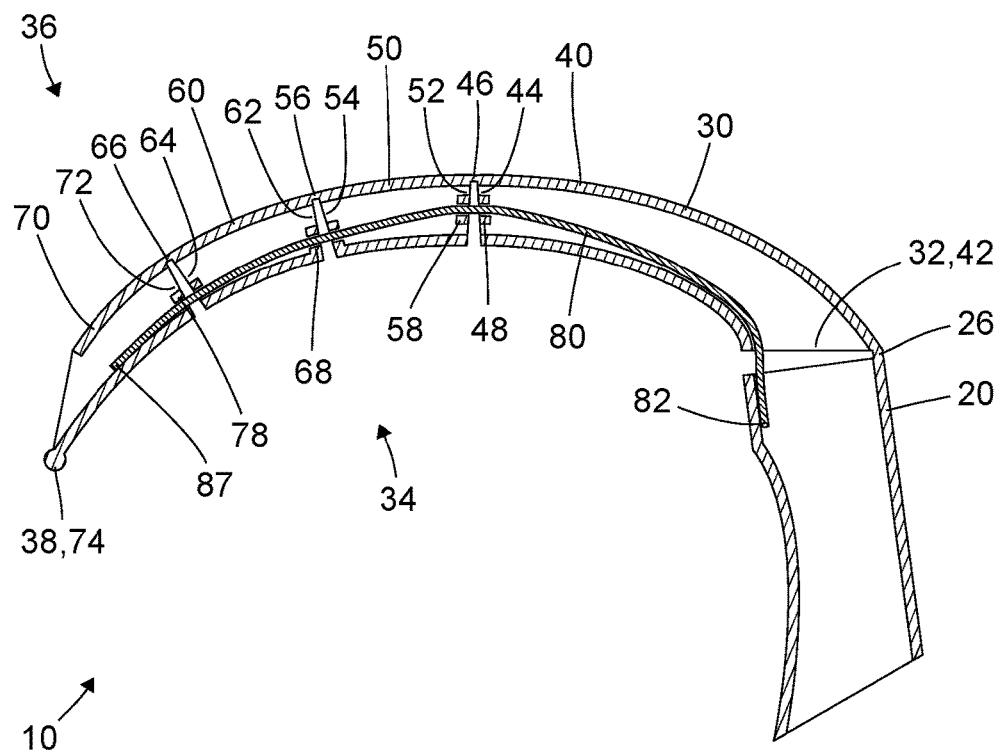
FIG. 8 is a schematic sectional view of a further laryngoscope.

FIG. 8 shows a schematic view of a section through a further laryngoscope 10 which, in terms of certain features, properties and functions, is similar to the laryngoscopes shown in FIGS. 1 to 7. The section plane of FIG. 8 corresponds to the section planes of FIGS. 2 to 7. Features, properties and functions of the laryngoscope in FIG. 8 that distinguish it from the laryngoscopes shown in FIGS. 1 to 7 are described below in particular.

The laryngoscope 10 shown in FIG. 8 differs in particular from the laryngoscope shown in FIGS. 1 to 4 in particular in that guiding structures 48, 58, 68, 78 in the form of eyelets at different spacings from the joints 46, 56, 66 are provided at the mutually facing ends 44, 52, 54, 62, 64, 72 of the elements 40, 50, 60, 70. In the example shown, two mutually opposite eyelets 48, 58, 68, 78 are always provided at mutually opposite ends 44, 52 or 54, 62 or 64, 72 of two adjacent elements 40, 50, 60, 70. In contrast to this, at each transition between two adjacent elements 40, 50, 60, 70, it is possible to provide only one guiding structure 48, 58, 68, 78 at an end 44, 52, 54, 62, 64, 72 of one of the two adjacent elements 40, 50, 60, 70.

The different spacings of the guiding structures 48, 58, 68, 78 from the joints 46, 56, 66 between the elements 40, 50, 60, 70 have the effect that a tensile force in the force-transmitting mechanism 80 generates different moments on the joints 46, 56, 66, which curve the blade 30. For example, the arrangement of the guiding structures 48, 58, 68, 78 indicated in FIG. 8 has the effect that a pivoting of the handle 20 relative to the proximal end 32 of the blade 30 influences the curvature at the third joint 66 more than at the second joint 56 and much more than at the first joint 46. It is thus possible, for example, to compensate for the fact that, during the intended use of the laryngoscope 10, the tongue base (near the distal end 38 of the blade 30) applies a greater force to the blade 30 than do other parts of the tongue, and that a force is intended to be exerted above all with the distal end 38 of the blade of the laryngoscope 10.

FIG. 9 shows a schematic view of a section through a further laryngoscope 10 which, in terms of certain features, properties and functions, is similar to the laryngoscopes shown in FIGS. 1 to 8. The section plane of FIG. 9 corresponds to the section planes of FIGS. 2 to 8. Features, properties and functions of the laryngoscope 10 in FIG. 9 that distinguish it from the laryngoscopes shown in FIGS. 1 to 8 are described below in particular.

The laryngoscope 10 shown in FIG. 9 differs in particular from the laryngoscopes shown in FIGS. 1 to 4, 7 and 8 in particular in that the force-transmitting mechanism 80 comprises a plurality of levers 91, 92, 93 which are connected to the handle 20, to one another and to the fourth element 70 by pull rods 94, 95, 96, 97 or other pulling elements with little elastic expansion. A first pull rod 94 couples the handle 20 to a first lever 91 in the first element 40. A second pull rod 95 couples the first lever 91 in the first element 40 to a second lever 92 in the second element 50. A third pull rod 96 couples the second lever 92 in the second element 50 to a third lever 93 in the third element 60. A fourth pull rod 97 couples the third lever 93 in the third element 60 to the fourth element 70.

A proximal end of the first pull rod 94, spaced apart from the lever 91, is mechanically connected to the handle 20 at a location spaced apart from the joint 26 between the handle 20 and the proximal end 32 of the blade 30. The distal end of the pull rod 97, directed away from the third lever 93, is connected to the fourth element 70 near the first side 34 at a location spaced apart from the joint between the third element 60 and the fourth element 70. In the example shown, the first lever 91 is configured as a buckled lever or angle lever, and the second lever 92 and the third lever 93 are configured as straight levers. The first lever 91, the second lever 92 and the third lever 93 are each articulated near the first side 34 of the blade 30 resting on the tongue of the patient during the intended use, and therefore at a distance from the joints 46, 56, 66 at the second side 36 of the blade 30.

The first lever 91 configured as an angle lever causes a deflection of the force transmitted by the force-transmitting mechanism 80. On account of different distances of the coupling sites of the pull rods 94, 95, 96, 97 from the pivot axes of the levers 91, 92, 93, all the levers 91, 92, 93 effect a conversion of a first force and of a first path proximally from the lever 91, 92, 93 into a second force and a second path distally from the lever 91, 92, 93. In the case free of friction, the ratio between the first force and the second force corresponds to the ratio between the second path and the first path. Pivoting movements of the elements 40, 50, 60, 70 relative to one another and of the levers 91, 92, 93 relative to the elements 40, 50, 60, hence varying pulling directions of the pull rods 94, 95, 96, 97, can change the conversion ratios effected by the levers 91, 92, 93.

Conversion by means of levers 91, 92, 93 or, in contrast to the view in FIG. 9, by pulleys or other gears within the force-transmitting mechanism 80 can, in the same way as in the laryngoscope shown in FIG. 8, can have the effect that a pivoting movement of the handle 20 relative to the proximal end 32 of the blade has an influence on the curvature of the blade 30 that varies along the blade 30. To put it another way, levers 91, 92, 93, 94 or other gears have the effect that a pivoting movement of the handle 20 relative to the proximal end 32 of the blade influences the curvature of the blade 30 at a first joint 46, 56, 66 more strongly or more weakly than at a second joint 46, 56, 66.

FIG. 10 shows a schematic view of a section through a further laryngoscope 10 which, in terms of certain features, properties and functions, is similar to the laryngoscopes shown in FIGS. 1 to 9. The section plane of FIG. 10 corresponds to the section planes of FIGS. 2 to 9. Features, properties and functions of the laryngoscope 10 in FIG. 10 that distinguish it from the laryngoscopes shown in FIGS. 1 to 9 are described below in particular.

In the same way as the laryngoscopes shown in FIGS. 1 to 9, the laryngoscope 10 shown in FIG. 10 has a handle 20 and a blade 30, of which the proximal end 32 is mechanically connected in an articulated manner to the handle 20 by a joint 26. A proximal portion 40 of the blade 30 is adjoined by a first chain of elements 140, 150, 160, 170 at the first side 34 resting on the tongue of a patient during the intended use of the laryngoscope 10. Moreover, the proximal portion 40 of the blade 30 is adjoined by a second chain of elements 240, 250, 260, 270 at the side 36 directed toward the palate of the patient during the intended use of the laryngoscope. The second chain of elements 240, 250, 260, 270 is substantially parallel to the first chain of elements 140, 150, 160, 170, wherein the spacing between both chains decreases in the distal direction. The outermost distal elements 170, 270 are mechanically connected to each other rigidly at their distal ends and form the distal end 38 of the blade 30.

Between the proximal portion 40 of the blade 30 and the elements 140, 150, 160, 170, 240, 250, 260, 270, joints are provided which, in the example shown, are configured as flexure bearings. Alternatively and in contrast to the view in FIG. 10, the joints between the 140, 150, 160, 170, 240, 250, 260, 270 can be configured as form-fit joints, for example with shafts or axle journals and corresponding bearing shells.

In the regions of the joints between adjacent elements 140, 150, 160, 170, 240, 250, 260, 270, the elements 140, 150, 160, 170, 240, 250, 260, 270 are moreover connected to one another by spacer components 350, 360, 370. One end 351, 361, 371 of each spacer component 350, 360, 370 is connected by a joint to the transition region between two adjacent elements 140, 150, 160, 170 at the first side 34 of the blade 30, and a second end 352, 362, 372 of each spacer component 350, 360, 370 is connected via a joint to the transition region between two adjacent elements 240, 250, 260, 270 at the second side of the blade 30. In the example shown, the joints at the ends 351, 352, 361, 362, 371, 372 of the spacer components 350, 360, 370 are configured as flexure bearings, although they can, in contrast to the view in FIG. 10, be configured for example as form-fit joints with shafts or axle journals in corresponding bearing shells.

If the outermost distal elements 170, 270 are of a rigid configuration, then, in contrast to the view in FIG. 10, the joints between these and the outermost distal spacer component 370 can be omitted.

In each spacer component 350, 360, 370, a guiding structure 358, 368, 378 is provided in the form of an opening or eyelet in which the force-transmitting mechanism 80 is arranged and guided. A guiding structure 48 is also provided at the distal end of the proximal portion 40 of the blade 30. In each spacer component 350, 360, 370 in the example shown, the ratio of the spacing of the guiding structure 358, 368, 378 from the first end 351, 361, 371 of the spacer component 350, 360, 370 at the first side 34 of the blade 30 and of the spacing of the guiding structure 358, 368, 378 from the second end 352, 362, 372 of the spacer component 350, 360, 370 at the second side 36 of the blade 30 is different from the ratio of the spacings of the guiding structure 48, at the distal end of the proximal portion 40 of the blade 30, from the first side 34 and from the second side 36 of the blade 30. These different ratios of the spacings have the effect that, by means of a pivoting of the handle 20 and the resulting movement of the force-transmitting mechanism 80, a deformation of the blade 30 can be brought about.

In all of the laryngoscopes 10 shown in FIGS. 1 to 10, the number of the elements 40, 50, 60, 70, 140, 150, 160, 170, 240, 250, 260, 270 can differ from the views shown in the figures. In contrast to the views in FIGS. 7 to 10, the force-transmitting mechanisms in these laryngoscopes can be configured to transmit pressing or shearing forces for enlarging the curvature of the blade 30. For this purpose, in particular in the laryngoscopes 10 shown in FIGS. 7 to 9, it is possible, in contrast to the views shown in FIGS. 7 to 9, for the joints 46, 56, 66 between the elements 40, 50, 60, 70 to be arranged not at the second side 36 but instead at the first side 34 of the blade 30, similarly to the laryngoscope shown in FIGS. 5 and 6.

While specific embodiments of the invention have been shown and described in detail to illustrate the application of the principles of the invention, it will be understood that the invention may be embodied otherwise without departing from such principles.

REFERENCE SYMBOLS 10 laryngoscope
20 handle of the laryngoscope 10
26 joint between the handle 20 and the proximal end 32 of the blade 30
30 blade of the laryngoscope 10
32 proximal end of the blade 30
34 side of the blade 30 intended to rest on the tongue and on the tongue base of a patient
36 side of the blade 30 to be directed toward the palate of a patient
38 distal end of the blade 30
40 first element of the blade 30, or proximal portion of the blade 30
42 proximal end of the first element 40
44 distal end of the first element 40
46 joint between the first element 40 and the second element 50
48 guiding structure at the first element or proximal portion 40, for guiding the force-transmitting mechanism 80
50 second element of the blade 30
52 proximal end of the second element 50
54 distal end of the second element 50
56 joint between the second element 50 and the third element 60
58 guiding structure at the second element 50, for guiding the force-transmitting mechanism 80
60 third element of the blade 30
62 proximal end of the third element 60
64 distal end of the third element 60
66 joint between the third element 60 and the fourth element 70
68 guiding structure at the third element 60, for guiding the force-transmitting mechanism 80
70 fourth element of the blade 30
72 proximal end of the fourth element 70
74 distal end of the fourth element 70
80 force-transmitting mechanism of the blade 20
82 proximal end of the force-transmitting mechanism 80
84 deflecting structure in the first element 40
85 flexure bearing between the deflecting structure 84 and the first element 40
87 distal end of the force-transmitting mechanism 80
91 first lever
92 second lever
93 third lever
94 first pull rod
95 second pull rod
96 third pull rod
97 fourth pull rod
140 first element of a first chain of elements
150 second element of the first chain of elements
160 third element of the first chain of elements
170 fourth element of the first chain of elements
240 first element of a second chain of elements
250 second element of the second chain of elements
260 third element of the second chain of elements
270 fourth element of the second chain of elements
350 first spacer component of the blade 30
351 first end of the first spacer component 350
352 second end of the first spacer component 350
358 guiding structure in the first spacer component 350
360 second spacer component of the blade 30
361 first end of the second spacer component 360
362 second end of the second spacer component 360
368 guiding structure in the second spacer component 360
370 third spacer component of the blade 30
371 first end of the third spacer component 370
372 second end of the third spacer component 370
378 guiding structure in the third spacer component 370

The invention claimed is:

1. A laryngoscope blade for an adaptable or adaptive laryngoscope, the laryngoscope blade comprising:
   a blade proximal end, which is articulatedly connected or articulatedly connectable to a handle for manual holding of the laryngoscope;
   a blade distal end for insertion into a throat of a patient during the intended use of the blade;
   a first side resting on a tongue of the patient during the intended use of the blade;
   a second side facing toward a palate of the patient during the intended use of the blade,
   a plurality of rigid elements which are arranged one after another in a longitudinal direction of the blade and which each extend from the first side of the blade to the second side of the blade;
   a plurality of joints, wherein each of the plurality of joints articulatedly connects two adjacent rigid elements of the plurality of rigid elements;
   a force-transmitting mechanism for transmitting a force, the force-transmitting mechanism having a force-transmitting mechanism proximal end and a force-transmitting mechanism distal end,
   wherein the force-transmitting mechanism distal end of the force-transmitting mechanism is mechanically connected to the blade distal end,
   wherein the force-transmitting mechanism, between the force-transmitting mechanism distal end and the force-transmitting mechanism proximal end, is movable relative to at least some of the rigid elements of the blade in a longitudinal direction of the force-transmitting mechanism,
   wherein the force-transmitting mechanism proximal end is configured to mechanically couple to the handle such that a pivoting of the handle relative to the blade proximal end moves the force-transmitting mechanism relative to the blade proximal end.

2. A laryngoscope blade according to the preceding claim, wherein
   the force-transmitting mechanism is arranged near the first side of the blade and is configured to transmit a tensile force, and one or more or all of the plurality of joints are arranged near the second side of the blade, or
   one or more or all of the plurality of joints are arranged near the first side of the blade, and the force-transmitting mechanism is arranged near the second side of the blade and is configured to transmit a pressing force.

3. A laryngoscope blade according to claim 1, wherein one or more or all of the plurality of elements have an annular cross section or a U-shaped cross section or a C-shaped cross section with respect to section planes orthogonal to the longitudinal direction of the blade.

4. A laryngoscope blade according to claim 3, wherein the force-transmitting mechanism is arranged inside a cavity at least partially enclosed by one or more or all of the plurality of elements.

5. A laryngoscope blade according to claim 1, further comprising:
   a guiding structure in one of the plurality of elements, for guiding the force-transmitting mechanism.

6. A laryngoscope blade according to claim 5, wherein the guiding structure comprises a channel or an eyelet.

7. A laryngoscope blade according to claim 1, further comprising:
   a deflecting structure on which the force-transmitting mechanism bears or to which the force-transmitting mechanism is mechanically connected or which is part of the force-transmitting mechanism, wherein the force-transmitting mechanism runs distally from the deflecting structure in a first direction and runs proximally from the deflecting structure in a second direction, which differs from the first direction.

8. A laryngoscope blade according to claim 1, wherein the force-transmitting mechanism has a converting mechanism which converts a first force and a first path proximally from the converting mechanism into a second force and a second path distally from the converting mechanism.

9. A laryngoscope blade for an adaptive laryngoscope, comprising:
   a blade proximal end, which is connected or connectable to a handle for manual holding of the laryngoscope;
   a blade distal end for insertion into a throat of a patient;
   a first chain of a plurality of elements which plurality of elements are arranged one after another in the longitudinal direction of the blade and which are each articulatedly connected in pairs, which chain extends from the proximal end as far as the distal end of the blade;
   a second chain of a plurality of elements which plurality of elements are arranged one after another in the longitudinal direction of the blade and which are each articulatedly connected in pairs, which chain extends from the proximal end as far as the distal end of the blade;
   a plurality of spacer components which each articulatedly connect a point at an element of the first chain to a point at an element of the second chain with a predetermined spacing;
   a force-transmitting mechanism for transmitting a force, with a force-transmitting mechanism proximal end and a force-transmitting mechanism distal end,
   wherein the force-transmitting mechanism distal end of the force-transmitting mechanism is mechanically connected to the blade distal end,
   wherein the force-transmitting mechanism, between the force-transmitting mechanism distal end and the force-transmitting mechanism proximal end, is movable relative to elements of the blade in the longitudinal direction of the force-transmitting mechanism.

10. A laryngoscope blade according to claim 9, further comprising:
    a guiding structure at one of the plurality of spacer components, for guiding the force-transmitting mechanism.

11. A laryngoscope blade according to claim 10, wherein
    a first guiding structure for guiding the force-transmitting mechanism is provided by the guiding structure at a first spacer component of the plurality of spacer components,
    a second guiding structure for guiding the force-transmitting mechanism is provided by the guiding structure at a second spacer component of the plurality of spacer components,
    a first ratio between the spacing of the first guiding structure from a first end of the first spacer component, which is directed toward the associated element of the first chain, and the spacing of the first guiding structure from a second end of the first spacer component, which is directed toward the associated element of the second chain, is different from a second ratio between the spacing of the second guiding structure from a first end of the second spacer component, which is directed toward the associated element of the first chain, and the spacing of the second guiding structure from a second end of the second spacer component, which is directed toward the associated element of the second chain.

12. A laryngoscope comprising:
a handle; and
a blade comprising:
a blade proximal end, which is articulatedly connected or articulatedly connectable to the handle for manual holding of the laryngoscope;
a blade distal end for insertion into a throat of a patient during the intended use of the blade;
a first side resting on a tongue of the patient during the intended use of the blade;
a second side facing toward a palate of the patient during the intended use of the blade;
a plurality of elements arranged one after another in a longitudinal direction of the blade;
a plurality of joints, wherein each of the plurality of articulatedly connects two adjacent elements of the plurality of elements;
a force-transmitting mechanism for transmitting a force, the force-transmitting mechanism having a force-transmitting mechanism proximal end and a force-transmitting mechanism distal end,
wherein the force-transmitting mechanism distal end of the force-transmitting mechanism is mechanically connected to the blade distal end,
wherein the force-transmitting mechanism, between the force-transmitting mechanism distal end and the force-transmitting mechanism proximal end, is movable relative to at least some of the rigid elements of the blade in a longitudinal direction of the force-transmitting mechanism,
wherein the force-transmitting mechanism proximal end is configured to mechanically couple to the handle such that a pivoting of the handle relative to the blade proximal end, moves the force-transmitting mechanism relative to the blade proximal end.

13. A laryngoscope according to the preceding claim, wherein
the proximal end of the blade is articulatedly connected or connectable to the handle,
the force-transmitting mechanism proximal end of the force-transmitting mechanism is coupled or couplable to the handle such that, by pivoting of the handle relative to the blade proximal end, a tensile force or a pressing or shearing force is applied to the force-transmitting mechanism.

* * * * *